United States Patent [19]

Peters et al.

[11] Patent Number: 5,063,205
[45] Date of Patent: Nov. 5, 1991

[54] UPTAKE OF IRON BY THE BODY

[75] Inventors: Timothy J. Peters, London; Kishor B. Raja, North Harrow, both of England

[73] Assignee: National Research Development Corporation, London, England

[21] Appl. No.: 130,594

[22] Filed: Dec. 8, 1987

[30] Foreign Application Priority Data

Jun. 5, 1987 [GB] United Kingdom ................. 8713169

[51] Int. Cl.$^5$ ...................... A61K 37/02; A61K 37/36
[52] U.S. Cl. ...................................... 514/12; 514/502; 514/814
[58] Field of Search .......................... 514/12, 502, 814

[56] References Cited

U.S. PATENT DOCUMENTS

| 3,036,917 | 5/1962 | Harrop ................................ 514/180 |
| 3,737,535 | 6/1973 | Brethour ............................ 514/180 |
| 4,362,710 | 12/1982 | Watanabe ............................ 514/502 |
| 4,786,599 | 11/1988 | Chessebeuf ....................... 435/240.3 |

FOREIGN PATENT DOCUMENTS

| 0134385 | 3/1985 | European Pat. Off. . |
| 0161817 | 11/1985 | European Pat. Off. . |
| 990868 | 5/1965 | United Kingdom . |
| 1123965 | 8/1968 | United Kingdom . |
| 1322102 | 7/1973 | United Kingdom . |
| 1417776 | 12/1975 | United Kingdom . |

OTHER PUBLICATIONS

Two (2) RHMA Feed Literature Compendium of Data Sheets for Veterinary Products, 1987–1988, 72 & 431–432.
"Lactase Helps Digestion of Milk" New Scientist, 27 Jun. 1985 Smith, "Expression of Digestive and Absorptive . . . " Ann. Rev. Physiol. 1985 47:247–260.
Bainter, K. et al., "The Effect of Triiodothyronine . . . " Arch Tier. Bd. 32 1982 H.p4 S.220–234, Berlin.
Malo, C. et al., "Influence of Epidermal Growth . . . " Gastroen. 1982:83:28–35.
O'Loughlin et al., "Effect of Epidermal Growth . . . " Am. J. Physiol. 249 G674–G678 1985.
Oka et al., "Effect of Mouse Epidermal Growth . . . " Endorinology 112:940, 1983.
Shotwell et al., "The Regulation of Neutral Amino Acid . . . " Biochimica et Biophysica Acta 737 (1983) 267–284.
Goodlad et al., "Intravenous but not Intragastric . . . " Gut 1987, 28, 573–582.
Goodlad et al., "Urogastrone-epidermal Growth . . . " Experientia 41(1985) 1161–1163.
Goodlad et al., "Effects of Systemic and . . . " Gut, 1985, 25, A 1154.
Goodlad et al.,"Effects of Intravenous and Intragastric . . . " J. Pathology, 1985 145, 97A.
Goodlad et al., "Intravenous but not Intragastric . . . " Regulator Peptides, 1984, 9, 332.
Menard et al., "Insulin Accelerates the Development . . . " Developmental Biology 1985, 150–155 (1981).
Celano et al., "Prenatal Induction . . . " Biochem. J. (1977) 162, 469–472.
Vaucher et al., "Maturational Effect . . . " J. of Pediatric Gastro. & Nutrition 427–432.
Henning, "Plasma Concentrations . . . " Am. J. Physiol. 4(5):E451-E-456 1978.
Hardy, "Absorption of Macromolecules from the Intestine . . . ".
Daniels et al., "The Influence of Exogenous . . . " J. Physio;. (1973) 681–695.
Daniels et al., "The Effect of Adrenalectomy . . . " J. Physiol. (1973) 229,697–707.
Malo et al., "Synergistic Effects of Insulin . . . " Biol. Neonate 44:177–184 (1983).
Henning, "Ontogeny of Enzymes . . . " Annual Rev. of Physiol. to be published May 1985.
Walker-Smith et al., "Intravenous Epidermal . . . " The Lancet Nov. 30 1985, 1239–1240.
Bjarnason et al., "Intestinal Permeability . . . " Gut 1985,26,579–585.
Simpson et al., "Mouse Intestinal $Fe^{3+}$ . . . " Biochimica et Biophysica Acta 856 (1986) 115–122.
Rudland et al., "Iron Salts & Transferrin . . . " Biochemical & Biophysical Re. Comm., vol. 75, No. 3, 1977, 556–562.
Partanen et al., "Epidermal Growth . . . " Dev. Biology 111,84–94(1985).
Forsbeck et al., "Subcellular Characterization of the Transferrin . . . " Acta path. Microbiol. Immunol. Scand. Sect . . . A, 94:245–252, 1986.
Laato et al., "Effect of Epidermal Growth Factor (EGF) . . . " Jour. of Surgical Research 41, 252–255 (1986).
Bomford et al., "Transferrin and Its Receptor . . . " Hepatology, vol. 5, No. 5, 1985, 870–875.
Mather et al., "The Growth of Mouse . . . " Exp. Cell Research 120 (1979) 191–200.
Perez-Infante et al., "Differential Regulation . . . " Endoc. 118, No. 1 383–392, 1986.
Raja et al., "In vitro Measurement . . . " Cell Biochem. & Function, vol. 5, 69–76(1987).
Anand, B. S. et al., "Absorption of Inorganic and Haemoglobin Iron in Coeliac Disease" British Journal of Heamatology, 1977, 37, 409–414.
Charlton, R. W. et al., "Iron Absorption" Ann. Rev. Med. 1983.34:55–68.

(List continued on next page.)

Primary Examiner—F. T. Moezie
Attorney, Agent, or Firm—Nixon & Vanderhye

[57] ABSTRACT

A method for the treatment of a patient comprises administering to said patient epidermal growth factor and an iron-providing material in order to effect an increase of the level of iron in the patient's bloodstream. The compositions may be administered parenteral, for example in intramuscular or oral form.

7 Claims, No Drawings

OTHER PUBLICATIONS

P. S. James et al., "Pig Enterocytes . . ." Jour. of Physio. 387, 36P, 1987.
P. S. James et al., "Selective Effects . . ." Jour. of Physio. 387, 41P, 1987.
P. S. James et al., "Dexamethasone Selectively . . ." Jour. of Physio. (1987) 393, pp. 569–582.
P. S. James et al., "Epiderma Growth . . ." Jour. of Physio. (1987) 393, pp. 583–594.
Raja et al., "Effect of Mouse . . ." Abstract Jul. 6–7/87, Med. Resear. Soc.
Baintner, "Intestinal Absorption . . ." CRC Press, Inc. Fla., USA pp. 7–120.

UPTAKE OF IRON BY THE BODY

This invention relates to the treatment of iron deficiency and in particular to pharmaceutical compositions and foodstuffs containing iron.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, in certain pathological conditions there is a malabsorption or maldistribution of body iron leading to a state of chronic anaemia. Such malabsorption or maldistribution is seen in certain intestinal disorders and in chronic diseases such as rheumatoid arthritis, certain haemolytic diseases and cancer.

Although a wide range of iron compounds is marketed for the treatment of iron deficiencies and the results thereof, and for the prophylaxis of such iron-deficiency states, the level of iron uptake by the body from these compounds is often quite low thereby necessitating the administration of relatively high dosage levels of the compound. The administration of high dose, poorly absorbed, iron complexes may cause siderosis of the gut wall and a variety of side effects such as nausea, vomiting, constipation and heavy malodorous stools.

It is therefore an object of the present invention to provide a means of enhancing the uptake of iron and it has been found that this may be achieved through the use of epidermal growth factor (EGF), usually through the incorporation into a pharmaceutical composition or a foodstuff of EGF. Although therapeutic applications of EGF have previously been described, for example in UK Patent 1,417,776 which describes the use of EGF in inhibition of the secretion of acidic gastric juice, there has never previously the secretion of acidic gastric juice, there has never previously been any indication that EGF had a role in the enhancement of iron uptake by the body.

According to the present invention a method for the treatment of a patient, particularly a human or other mammalian patient, comprises administering to said patient epidermal growth factor and an iron-providing material in order to effect an increase in the level of iron in the patient's bloodstream.

The present invention extends to the use of EGF to enhance iron uptake from a wide variety of iron-providing materials, which may contain iron in the ferrous or particularly the ferric form, in both humans, animals and birds. Particular interest centres on the treatment of mammals, especially humans and also pigs, for example piglets.

The iron-providing material may be any physiologically acceptable substance capable of raising the level of iron in the bloodstream on administration in vivo, including both iron salts and iron complexes. Examples of specific iron-providing materials include, particularly for human use, ferric chloride, ferric ascorbate, ferric citrate, ferrous fumarate, ferrous gluconate and ferrous succinate, and, particularly for use in piglets, compounds, including some of those mentioned above, which are described in UK Patent 1,322,102 and U.S. Pat. No. 4,362,710, for example iron (ferric) dextran, ferrous fumarate and ferric citrate. Also of particular interest for both human and animal use are the iron complexes which are the subject of UK Patents and Patent Applications 2117766B, 2136806A, 2157686A and particularly 2128998B, especially (3-hydroxy-2-methyl-4-pyrone)$_3$ iron(III) and related homogeneous and heterogeneous 3:1 hydroxypyrone:iron(III) complexes.

The EGF may be administered alone in order to enhance iron uptake from either normally ingested or specifically administered iron-providing materials and in the latter aspect the present invention therefore includes a product comprising epidermal growth factor and an iron-providing material for simultaneous, separate or sequential use in growth promotion, for example a kit comprising the two components in association. However, it will most usually be formulated together with an iron-providing material and the present invention therefore includes a product comprising an iron-providing material and epidermal growth factor for use in therapy.

The EGF used in the present invention may conveniently be derived from various natural sources, particularly mammalian sources, since the active sequence thereof is closely conserved among species. Alternatively, synthetic EGF may be used that may optionally have variations in the molecule, within the active sequence or particularly outside it, which do not correspond to those found in nature or which constitute an admixture of variations found in different species in nature. Essentially any compound expressing the activity of the natural hormone may be used. The term epidermal growth factor is therefore used herein in a general sense to include all such natural materials and their synthetic equivalents, as well as variants thereon retaining the physiological activity of the molecule. Specific sources include mouse, rat, rabbit, cattle, goat, sheep, horse, pig and human EGF (urogastrone). In principle, EGF of the same species as the recipient is to be preferred and pig and human EGF are therefore of particular interest. Also of some especial interest is mouse EGF which has been produced by genetic engineering, although this technique could also be applied to the production of pig and human EGF, etc, the terms pig EGF and mouse EGF, for example, being used in a general sense once again to include the natural material and its synthetic equivalent, as well as variants thereon retaining the physiological activity of the molecule. The structure of mouse EGF is shown in UK Patent 1,417,776 and examples of possible active variants of the natural structure are also shown therein illustrating the type of variation which may also be applied with EGF derived from other sources whilst retaining activity.

EGF may be used according to the present invention for the manufacture of medicaments having a variety of forms. Usually, however, these will comprise, in addition to the EGF and an iron-providing material, a physiologically acceptable diluent or carrier. The present invention therefore includes a pharmaceutical composition comprising an iron-providing material, epidermal growth factor and a physiologically acceptable diluent or carrier.

The iron-providing material and the EGF may be formulated together in a pharmaceutical composition by a variety of methods. For instance, they may be applied as an aqueous, oily or emulsified composition incorporating a liquid diluent which may often be employed in injectable form for parenteral administration and therefore may conveniently be sterile and pyrogen free. For certain other uses a diluent which is sterile but not necessarily pyrogen free may be appropriate. As regards liquid diluents or carriers therefore, there is often particular interest in those which are sterile. Oral administration is often preferred for the treatment of iron deficiency anaemia in humans and the present invention is suited to such a route of administration. Although compositions incorporating a liquid diluent may be used for oral administration, it is more usual, at least in humans, to use compositions incorporating a solid carrier, for example a conventional solid carrier material such as starch, lactose, dextrin or magnesium stearate. Such solid compositions may conveniently be of a formed type, for example as tablets, capsules (including spansules), etc.

As indicated, liquid compositions are of particular interest in relation to parenteral administration, a requirement for which arises with humans in certain contexts but also particularly in a veterinary context, for example with pigs. The problems of iron deficiency anaemia in newly born pigs arise primarily during the first three weeks or so of their life when a very rapid weight gain takes place. The usual routes for administration of iron-providing materials to young piglets in the context of the present invention are parenteral, for example intramuscular, or oral, for example as a liquid preparation "injected" into the mouth. However, an alternative approach is to enhance the iron content of the milk on which the piglets are feeding by treating the mother pig using oral or parenteral administration, for example with an injectable slow release preparation (such an approach may also be of interest in a human context). As indicated previously, slow release preparations for the parenteral administration of EGF are of particular interest in view of the short half life of EGF in vivo when given by such a route (about 2½ minutes when given intravenously).

Other forms of administration than by injection or through the oral route may also be considered in both human and veterinary contexts, for example the use of suppositories or pessaries, or of compositions for buccal or nasal administration. Further details regarding the formulation of iron-providing materials are to be found in the patents relating to such compounds mentioned hereinbefore.

The compositions may be formulated in unit dosage form, i.e. in the form of discrete portions containing a unit dose, or a multiple or sub-unit of a unit dose. The dosage of the iron-providing material will of course depend on the particular material which is used but it may be indicated by way of guidance that the daily requirement of iron for the adult human is generally regarded as being from 2 to 4 mg and that the dosage is therefore that which is appropriate to ensure this level of intake. Further information on the dosage levels of the iron compounds is to be found in the ABPI Data Sheet Compendium published annually by Datapharm Publications Ltd., London, U.K., and in the various patents and patent applications mentioned hereinbefore. As regards the EGF, dosage will again depend on the particular iron-providing material to be used in conjunction with the EGF but, as a guide, it may be stated that an appropriate range is from 1.0 to 100 in terms of n.moles EGF/n.mole iron present in the material. The appropriate ratio will of course depend on the efficiency of the material as an iron provider in vivo and ratios both below and above those quoted may be considered. By way of further guidance it may be stated that in the context of the present invention a daily dosage of EGF of 10 to 100 n.moles/kg of body weight is often appropriate, although once again doses outside this range may be considered.

In addition to its use in pharmaceutical compositions the incorporation of EGF into foodstuffs may be considered, usually those already containing a source of iron. Such foodstuffs may take various forms, either liquid, semi-solid or solid, and may for example take the form of conventional human infant or piglet feed materials. Further examples of such piglet feed materials are to be found in the U.S. Pat. No. 4,362,710 referred to hereinbefore.

The present invention thus further includes a foodstuff which comprises epidermal growth factor and an iron-containing nutritional material.

The present invention further extends to the use of EGF in conjunction with members other than iron of the group of fifteen trace elements essential for human and animal well being. Many of these are transition elements and apart from iron other metallic trace elements of particular interest are chromium, and also manganese, cobalt, copper and molybdenum, as well as selenium and zinc. EGF may be used to enhance the uptake of the trace elements and effect an increase in the level of the element in the patient's bloodstream, particularly of cobalt, copper, selenium and zinc, in an essentially similar manner to that described herein for its use in the enhancement of the uptake of iron. Thus, pharmaceutical compositions and foodstuffs may be used containing EGF and a material providing one of these other trace elements or a plurality of materials providing different elements. Such materials may conveniently be chosen from those described in the art for providing the element in question and the pharmaceutical composition or foodstuff may conveniently, particularly in the case of a foodstuff, contain materials providing a range of these beneficial trace elements, including iron. Data on preferred human and veterinary dosage levels for the different elements is to be found in the literature but the use of daily dosages of EGF selected within the ranges quoted herein together with proportions of EGF and the element in question within the range quoted herein for iron will usually be broadly suitable.

The invention is illustrated by the following Example.

EXAMPLE: ENHANCEMENT OF UPTAKE OF IRON IN MICE (A) Six week old, male To mice received doses averaging 1 n.mole/day of mouse epidermal growth factor in their drinking water during a period of up to 7 days, a control group of similar mice receiving plain drinking water. Iron absorption was then studied in the mice by both in vitro and in vivo techniques. The former, using techniques as described by Raja et al, Cell Biochem. and Funct., 1987, 5, 69–76, involved incubation of intestinal fragments from the mice with a 0–450 $\mu$M solution of a $Fe^{3+}$ chelate (the 2:1 nitrilotriacetate:iron(III) complex) whilst the latter, using techniques as described by Simpson and Peters, Biochim. Biophys. Acta., 1986, 856, 115–122), involved instillation of 50–100 $\mu$l of a 250 $\mu$M solution of the $Fe^{3+}$ chelate into a tied-off loop of intestine of an anaesthetised mouse.

It was found that neither group showed a change in the wet weight of the duodenum per unit length but that cell turnover rates, as reflected by L-ornithine decarboxylase activity, were elevated in the duodenum of the animals which had received EGF. In vitro uptake studies also showed no change in the kinetic parameters for $^{59}Fe^{3+}$ uptake for EGF-treated animals [$K_m=101\pm18(4)$; $V_{max}=9.4\pm1.1(4)$ pmol/mg/min] as compared with the controls [$K_m=103\pm20(9)$; $V_{max}=10.5\pm0.9(9)$]. In vivo experiments showed a progressive increase in the total mucosal uptake of $^{59}Fe^{3+}$ in the EGF-treated animals which was maximal after 3 days of EGF administration. The data obtained is shown in the Table from which it will be seen that the enhanced uptake was due to increases in both the mucosal retention and carcass transfer.

In vivo studies were carried out with $^{51}Cr$-EDTA (ethylene diamine tetra-acetic acid) using techniques as described by Bjarnason et al, Gut, 1985, 26, 579–586 which involve instillation of 50–100 μl of a 100 μM $^{51}Cr$-EDTA solution into a tied-off loop of intestine of an anaesthetised mouse. These showed an increased permeability in EGF-treated animals [total mucosal uptake=25.1±1.7(5) pmol/mg/10 min] as compared with the controls [total mucosal uptake=9.6±1.1(5) pmol/mg/10 min; $p<0.001$].

These studies demonstrate that oral EGF feeding enhances intestinal proliferation and in vivo $^{59}Fe^{3+}$ absorption, although the latter is not via a specific carrier-mediated pathway.

TABLE[1]

|  | Mucosal retention | Carcass transfer | Total mucosal flux |
|---|---|---|---|
| Controls (20) | 40.6 ± 2.3 | 22.9 ± 2.0 | 63.4 ± 3.4 |
| EGF-treated | 57.1 ± 6.3[2] | 35.3 ± 2.6[2] | 92.4 ± 8.4[3] |

[1] Values are for mean ± SE pmol $^{59}Fe^{3+}$/mg tissue/10 minutes for number of animals indicated between parentheses.
[2] $p < 0.01$
[3] $p < 0.001$ (B) The procedure described under (A) was repeated but with the treated mice receiving the EGF for 3 rather than 7 days. After fasting for 12 hours both the EGF-treated and the control mice were treated intragastrically with 1 μCurie of $^{59}Fe^{3+}$ administered as 50 μl of a 100 μM aqueous solution of the radiolabelled 2:1 nitrilotriacetic acid:iron(III) complex. The mice were subjected to a whole body count by gamma counting at 3 hours and 7 days later. The percentage of the $^{59}Fe^{3+}$ present at 3 hours which was retained after 7 days was 12.9±2.0 for the controls and 21.0±3.2 for the EGF-treated mice thereby clearly indicating a markedly increased retention for the treated mice.

We claim:
1. A method for the enhancement of iron uptake or the treatment of iron deficiency in a subject in need thereof which comprises administering to said subject amounts which together are therapeutically effective of epidermal growth factor (EGF) and an iron providing material.
2. A method according to claim 1, in which the EGF is administered in a proportion of 1.0–100 n.moles EGF/n.mole of iron administered.
3. A method according to claim 1, in which the EGF and iron providing material are administered in unit dosage form.
4. A method according to claim 1, which is used for the treatment of the human.
5. A method according to claim 2, which is used for the treatment of the piglet.
6. A method according to claim 1, in which the epidermal growth factor is mouse EGF.
7. A method according to claim 4, in which the epidermal growth factor is human EGF.

* * * * *